United States Patent [19]
Halperin et al.

[11] Patent Number: 5,810,735
[45] Date of Patent: Sep. 22, 1998

[54] EXTERNAL PATIENT REFERENCE SENSORS

[75] Inventors: Louis E. Halperin, St. Paul; James K. Carney, Eden Prairie; Robert C. Beck, St. Paul, all of Minn.; Michael Turi, Wood-Ridge, N.J.

[73] Assignee: Medtronic, Inc., Minneapolis, Minn.

[21] Appl. No.: 848,764

[22] Filed: May 1, 1997

Related U.S. Application Data

[63] Continuation of Ser. No. 402,681, Feb. 27, 1995.
[51] Int. Cl.$^6$ ....................................................... A61B 5/02
[52] U.S. Cl. ............................................ 600/486; 128/899
[58] Field of Search ........................................ 128/847–899, 128/903; 607/27; 600/301, 483–486, 509, 511, 522

[56] References Cited

U.S. PATENT DOCUMENTS

| | | |
|---|---|---|
| 4,016,764 | 4/1977 | Rice . |
| 4,023,562 | 5/1977 | Hynecek et al. . |
| 4,257,423 | 3/1981 | McDonald et al. . |
| 4,407,296 | 10/1983 | Anderson . |
| 4,432,372 | 2/1984 | Monroe . |
| 4,485,813 | 12/1984 | Anderson et al. . |
| 4,519,401 | 5/1985 | Ko et al. ............................ 128/903 X |
| 4,556,063 | 12/1985 | Thompson et al. . |
| 4,750,495 | 6/1988 | Moore et al. . |
| 4,858,615 | 8/1989 | Meinema . |
| 4,886,064 | 12/1989 | Strandberg ........................ 128/903 X |
| 4,967,755 | 11/1990 | Pohndorf . |
| 5,127,404 | 7/1992 | Wyborny . |
| 5,324,326 | 6/1994 | Lubin . |
| 5,411,535 | 5/1995 | Fujii et al. ........................ 128/903 X |
| 5,460,183 | 10/1995 | Raynes et al. ........................ 128/673 |

FOREIGN PATENT DOCUMENTS 9413200   6/1994   WIPO .

OTHER PUBLICATIONS

Ko et al., "A Designof Capacitive Pressure Transducer", IEEE Proc. Symp. Biosensors, 1984, p. 32.
Graeger et al., "A ceramic differential–pressure transducer", Phillips Tech. Rev., 43:4:86–93, Feb. 1987.
Advertisement in Road Runner Sports, AVOCET Alpine Vertech Watch, p. 42.
Jones et al., "The design and some appications of sensitive capacitance micrometers" *Journal of Physics E: Scientific Instruments*, 1973, vol. 6, p. 589.
Dias et al., "Capacitive Blood Pressure Transducer", *ISA Transactions*, vol. 19, No. 3, p. 19.
Chau et al., "An Ultraminiature Solid–State Pressure Sensor for a Cardiovascular Catheter", *Microsensors, IEEE Press*, p. 343, 1991.
Transducers, Chapter 4, Capacitive Transducers, p. 89, 1974.

*Primary Examiner*—John P. Lacyk
*Assistant Examiner*—Samuel Gilbert
*Attorney, Agent, or Firm*—Harold R. Patton; Michael B. Atlass

[57] ABSTRACT

A system for long term monitoring of an internal patient medical parameter having an external reference and means to correct the internal measurements of the parameter via external measurements taken by the external reference. A coordinating device makes the correction and makes available a histogram-based record of the parameter over time. This information can be used to reprogram an implantable device or for other therapeutic or diagnostic purposes. Pressure sensor embodiment is detailed.

14 Claims, 6 Drawing Sheets

EXTERNAL PATIENT REFERENCE SENSORS

This application is a continuation of copending application Ser. No. 08/402,681 filed on Feb. 27, 1995 and which designated the U.S.

REFERENCE TO RELATED APPLICATIONS

Reference is hereby made to commonly assigned, co-pending U.S. patent application Ser. Nos. 08/394,870 and 08/394,860 (Docket Nos. P-3508 and P-3737) filed on even date herewith for IMPLANTABLE CAPACITIVE ABSOLUTE PRESSURE AND TEMPERATURE SENSOR and IMPLANTABLE CAPACITIVE PRESSURE AND TEMPERATURE MONITOR SYSTEM, respectively, which describe a monitoring system and sensor used with the presently most preferred embodiment of this invention.

BACKGROUND OF THE INVENTION

This invention relates to the field of medical monitoring devices generally and has particular application in the field of chronic or long term patient monitoring particularly for pressure sensing. There are many situations in which a patient requires long term monitoring and when it may be desirable to implant a sensor for monitoring within the patient's body. Such a sensor needs to be checked against an external reference for accuracy on an ongoing basis. This is particularly important in the area of pressure sensing where an implanted pressure sensor within the body is subjected not only to the changes in pressure within the body and the location at which the sensor is implanted but also to the ambient pressure or barometric pressure in which the patient is located. For example, if the patient were to be riding in a car up a mountain or travelling up or down a large building in an elevator the local barometric pressure around the patient would change affecting the physiological measurements of the changes in pressure registered by the implanted pressure sensor/monitor device.

Because of these problems, long term absolute pressure monitoring of patients through implantable sensors has not been done before.

There is in the acute or short term pressure sensor field two types of devices which have been employed generally in hospitals and critical care facilities.

A Millar catheter contains a silicon-based pressure sensor at the tip of a flexible catheter which is inserted into the patient's body at the point where pressure is to be measured (for example the right ventricle or pulmonary artery). Readings from the Millar-type sensor are corrected for atmospheric ambient changes using a barometer in the same room.

A second system for measuring internal pressures consists of a fluid-filled catheter with a diaphragm at one end and a pressure sensor at the other end. The diaphragm is placed at the point inside the body where pressure is to be measured. The internal pressure is transmitted up the catheter through the incompressible fluid and is measured by the pressure sensor outside the body. The effects of barometric pressure are eliminated by placing the two ends of the catheter at the same height above the floor.

Barometric pressure readings are of course widely available through various devices. Recently, watch companies have even begun to supply small barometric pressure sensors in association with their watches. For example, Avocet provides a watch (the "AOU-OZ Alpine Vertech) which will describe the height at which one is located above sea level based on the pressure reading at that location, and has other functions related to mountain climbing that use the on-board pressure and temperature sensors.

Chronically implanted dynamic sensors have been reported but they cannot measure a baseline or DC pressure (gauge pressure). They do not have a frequency response at DC and therefore do not maintain a stable zero point. They can and do provide for good waveforms of dynamically changing pressures, but the absolute value of the pressure measure is unknown.

Numerous low cost barometric pressure measuring circuits exist in the art. Some are illustrated in the proceedings of the Second Annual Portable by Design Conference sponsored by Electronic Design Magazine (Feb. 13/17, 1995) Santa Clara, Calif.

There has developed a need to monitor pressure or other metrics with a device implanted into the body of a patient that can be corrected for by changes to barometric pressure reference or to an external measurement of the same metric. This invention particularly addresses the problem of allowing for changing external ambient conditions (particularly pressure) and adjusting for their effects on implanted monitoring sensors.

SUMMARY OF THE INVENTION

A preferred form of the invention is a system consisting of implanted sensor, external reference and apparatus to combine the readings. The readings can be used to adaptively reconfigure or change the functioning of the implanted device, automatically or with medical oversight through human analysis of displays or printouts of long term readings. The invention employs a wearable or otherwise external barometric pressure sensor and monitoring apparatus to produce and store a set of barometric measurements or pressure readings associated with particular times. A temperature corrected reading may be preferred. This external pressure sensor may be mounted in a housing carried by an individual. He or she could wear it for example on the wrist or in a belt, or in a purse, so that it will go where the individual goes and therefore be subject to the same ambient pressure environment that the individual is subjected to. Within the housing, a sensor reads the ambient barometric pressure and these pressure readings are coordinated with time such that when they are read out these readings or measurements can be paired with measurements made by an internal/implanted body sensor tracking the pressures within the body of the patient at approximately those same times.

In its presently preferred form it would be most useful to have the data from the implantable device telemetered to a programmer or other similar computer device which would coordinate data regarding pressure taken from the implanted device with the data developed and recorded by the external sensor. This recorded and coordinated data can then be used by the programmer (or other computerized device) to generate physiologic measurement readings, or in other words, to calibrate or adjust the implanted device readings. These adjusted readings can then be used by a physician to provide further therapy for the patient, whether by changing the functioning of the implanted device or by use of drug or other therapies. The readings could also be used to produce histograms of patient health with respect to the measured parameter which may be used for many purposes that would naturally occur to the reader. The corrected measurements or readings could also be used to automatically change the functioning of the implanted device if desired. This last potential use of this invention can make the implanted apparatus associated with the implanted sensor responsive to changing patient conditions with respect to the measured parameter over time or to adaptively select between available therapies that can be accomplished by the implanted device when enough data has been gathered.

A form of the invention that does not necessarily require historical data would have the implanted device communicate directly with the external reference sensor device to coordinate the readings without the use of a "programmer" computer. In such a configuration direct communications would need to be established between the internal and external devices, and the external device would be best configured in a wearable housing.

DETAILED DESCRIPTION OF A PREFERRED EMBODIMENT OF THIS INVENTION

Figure 1:
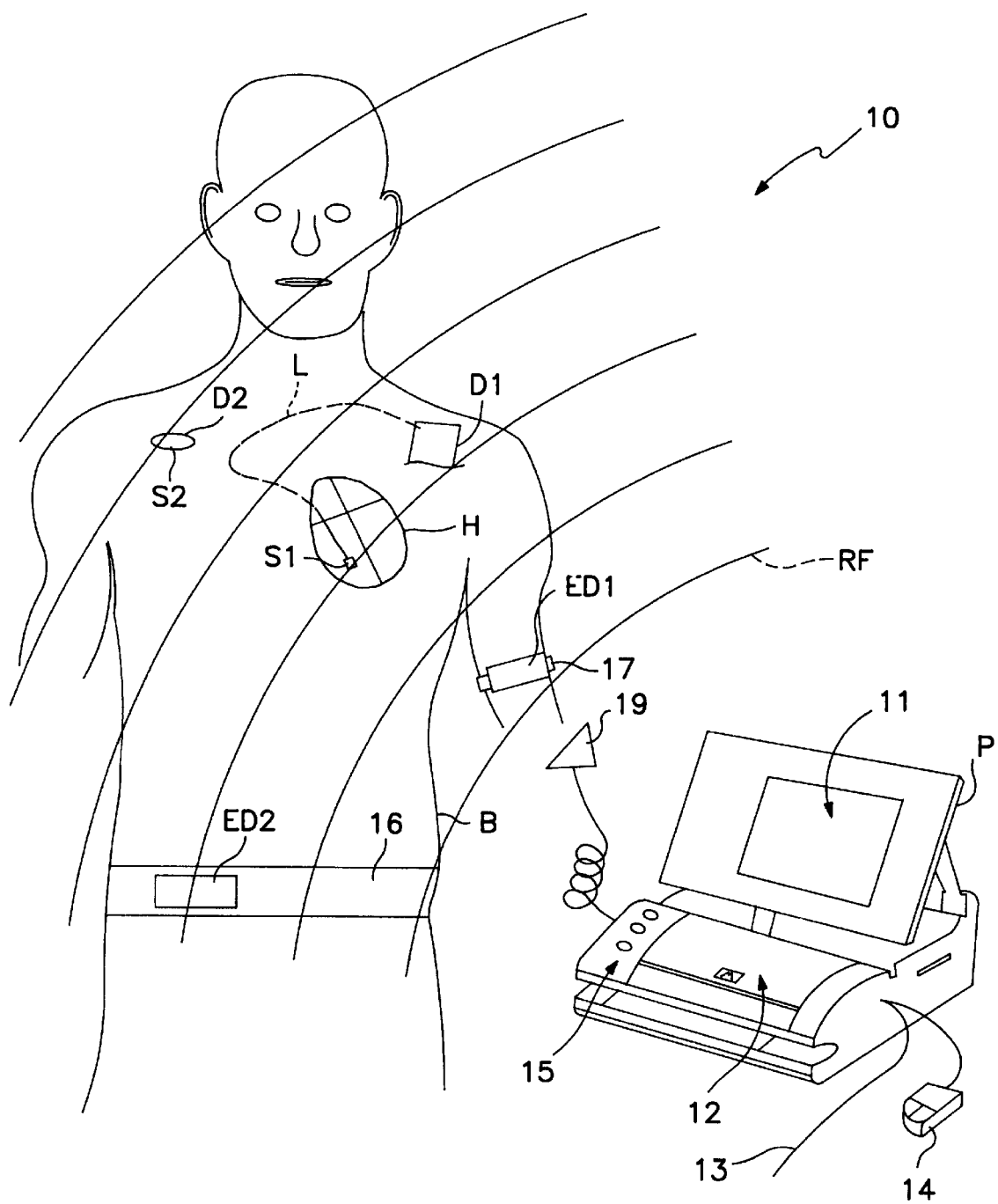
FIG. 1 is an illustration of a human body having implanted and wearable devices in association with a programmer.

For purposes of description, refer first to FIG. 1 in which preferred embodiments of the system 10 is described in detail as follows.

The human body B may have various implanted devices having sensors which react or are affected by the ambient environment in which the patient's body B is located. For purposes of illustration, two such devices $D_1$ and $D_2$ are shown. Device $D_1$ illustrates an implantable device which could be, for example, a cardiac stimulator or other device, having at least one lead connected to a sensor $S_1$ which is implanted within the heart H. In the presently most preferred embodiment, this sensor $S_1$ would be a ventricular pressure sensor which can be quite useful for diagnostics and for determining long term patient cardiac care.

An alternative device $D_2$ (which at the present time would not be assumed to be in the same body B as device $D_1$), has associated with it a sensor $S_2$. External devices such as $ED_1$ and $ED_2$ are also illustrated here connected to belts 17 and 16, respectively.

It is left to the imagination of the reader of ordinary skill in this art as to where other implantable devices of the kind $D_x$ and external devices of type $ED_x$ may be located. Such placement configuration is only limited for this invention by the claims as set forth at the end of this specification.

Also in system 10 is the programmer device P. This device is primarily a general purpose computer system with an RF transmitter/receiver that can communicate with the implanted devices $D_x$ and the external devices $ED_x$. (Wave RF shown here emanating from the programmer P.) In some presently preferred embodiments, a communications pad such as pad 19 may be connected directly to the programmer P to be located in close association with the implanted device so as to minimize the interference associated with telemetry between the programmer P and the implanted device $D_x$. Also, a separate communications port or channel can connect the external device to the programmer if desired, rather than using an RF connection.

As is known, various methods for programming and modifying a program by a user through the external programmer P have developed including a light pen 13, mouse input device 14, keyboard (under panel 12), function keys 15 and touch sensitive screen 11.

Figure 2:
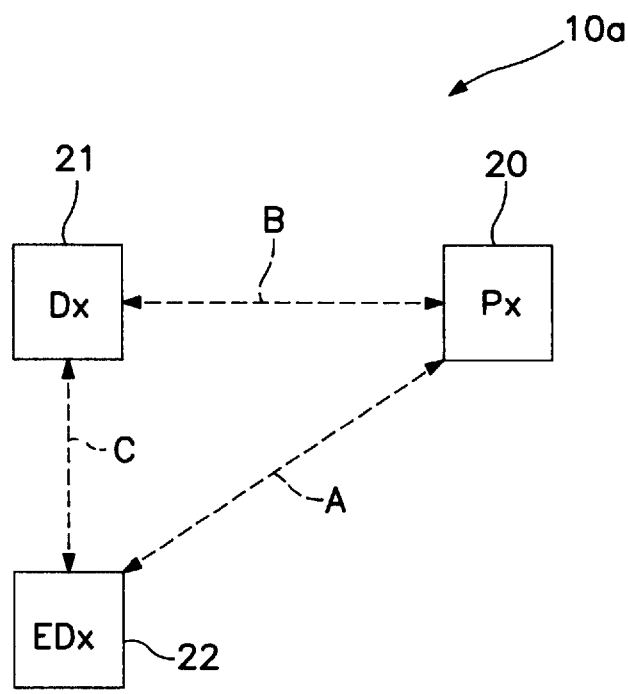
FIG. 2 is heuristic block diagram of preferred embodiment device communications configurations.

Referring now to FIG. 2, the communications system for system $10_a$ is described in a heuristic block diagram. The components of such a system include a programmer $P_x(20)$, a implanted device $D_x(21)$ and a external device $ED_x(22)$. Communications pathways exist between the programmer 20 and implanted device 21 as illustrated by broken line B; between the programmer and the external device 22 as illustrated by broken line A; and the external device and internal device as illustrated by broken line C. Not all of these communication pathways are required at all times. In accord with the presently preferred embodiment of this invention using an absolute pressure sensor as the implanted device sensor, no communication pathway exists between the implanted device 21 and the external sensor device 22. Therefore the diagram would not include broken line C for such a configuration.

Because the presently preferred embodiment does not include a communications pathway C, the coordination of the timing of events between the recording of pressure sensing in device 21 and device 22 is accomplished in the programmer 20 by means of an initialization and uplink procedure described in detail later with reference to FIG. 5. The preferred communications pathway A may be a direct hard wired link between the programmer and the external device, say for example using a RS 232 configured cable. In almost all situations, it will be difficult not to use RF as the communications pathway between the implanted device 21 and the external devices 20 or 22. However, it is not outside the scope of this invention to employ communications devices such as those described by Funke in U.S. Pat. No. 4,987,897, describing a body buss in which the entire human body is used as a communications pathway for electrical signals between devices within and external to but associated electrically with the body of the patient. Other communications pathways including optical based means may be established as needed or desired by the designer.

Figure 3:
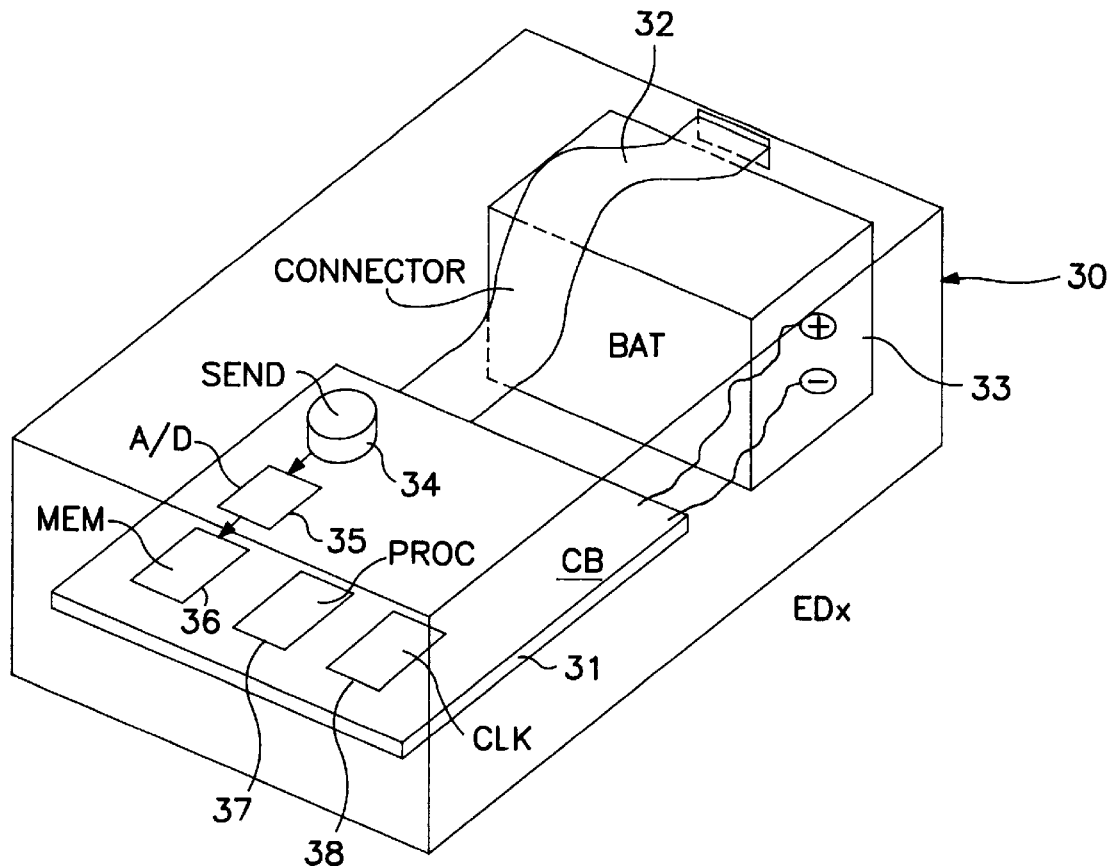
FIG. 3 is a perspective diagram with a cutaway showing parts and configuration for an external device in accord with a preferred embodiment of this invention.

Referring now to FIG. 3, an external device $ED_x$ is illustrated having a housing 30 having internal thereto a circuit board 31, a battery 33, and a cable for connector 32 connecting the circuit board to the programmer type device (like P of FIG. 1) when plugged in. In the presently preferred embodiment, this connector is an RS 232 cable. The circuit board has associated with it certain main components including a barometric pressure sensor 34, and Analog to Digital (A/D) convertor 35, a memory 36, a processor 37 and a clock 38. These components are interconnected electrically via the circuit board 31 to provide signal pathways to perform the functions described herein.

The presently most preferred sensor for use as a sensor 34 is available from a Luca Nova Sensor, Fremont, Calif. and it is a silicon-based diaphragm pressure sensor with a sensitivity of ±0.05 mm Hg. A pressure sensor of similar sensitivity should be mounted in the implanted device to generate easily convertible readings but any reasonable sensor pair may be used with appropriate correction algorithms as can be easily surmised by one of ordinary skill in this field.

Memory requirements for memory 36 depend upon the length of time and the size of the data word to be stored relative to the measurements being taken and, also depends upon the number of measurements that will be kept. These determinations may be made on an individual basis depending on the needs of the patient. For example, if a six month period of monitoring is to be undertaken before the calibration and reconciliation of the two sensors is to be accomplished, and measurements are taken and stored once every hour the memory size minimum would be 24 hours× 31 days×6 months×number of bits per measurement datum. Compression techniques, averaging and other algorithms may be used as well to reduce the amount of storage required. Generally less than 200k bytes is needed for most applications of pressure sensing.

In general, the battery 33 powers the components on the circuit board including at least those mentioned previously. The clock 38 provides a reference point so that the sensor 34 data converted by the A/D converter 35 can be stored in memory in a way that is associated (in a time related way) with the way memory is used to record sensor measurements by the implanted device. An on-board processor 37 can be employed to execute various algorithms for manipulating or encoding the data as desired by the user. A connector 32 allows for the transfer of data from the memory to an off the board programmer or other computer although RF or other connections (not shown) can be made instead for this purpose.

Figure 4:
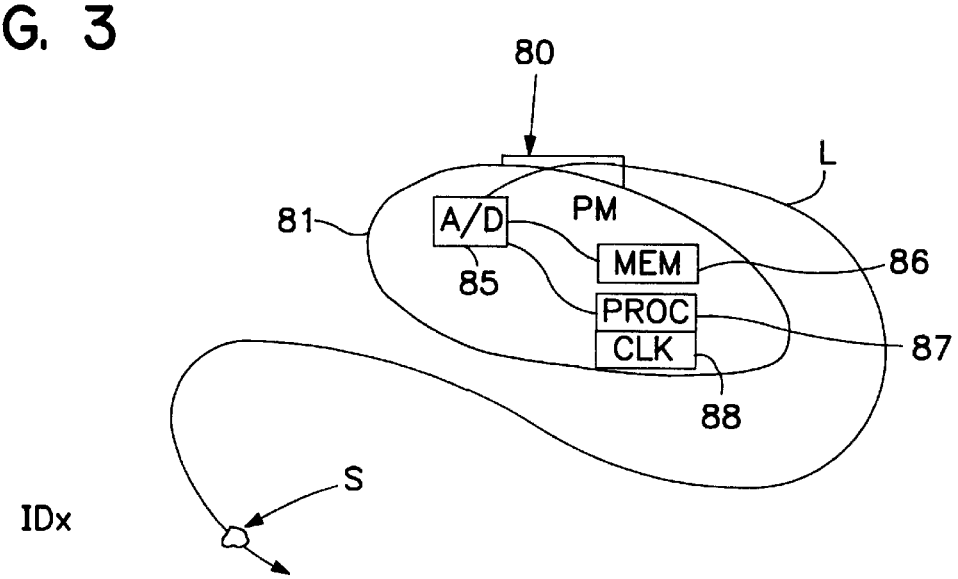
FIG. 4 is a representational diagram of an implantable device as used in accord with a preferred embodiment of this invention.

Referring now to FIG. 4, in which an implantable device is illustrated having associated lead L and sensor S for connection in this case to the ventricular area of the right ventricle of a patient's heart. The body 81 of the implantable device 80 contains an A/D converter 85 connected to the lead L for converting analog signals from sensor S for processing by processor 87 and for storage in the memory 86 and associated time related coordination data facilitated and enabled by the timing signals from a clock 88.

Figure 5:
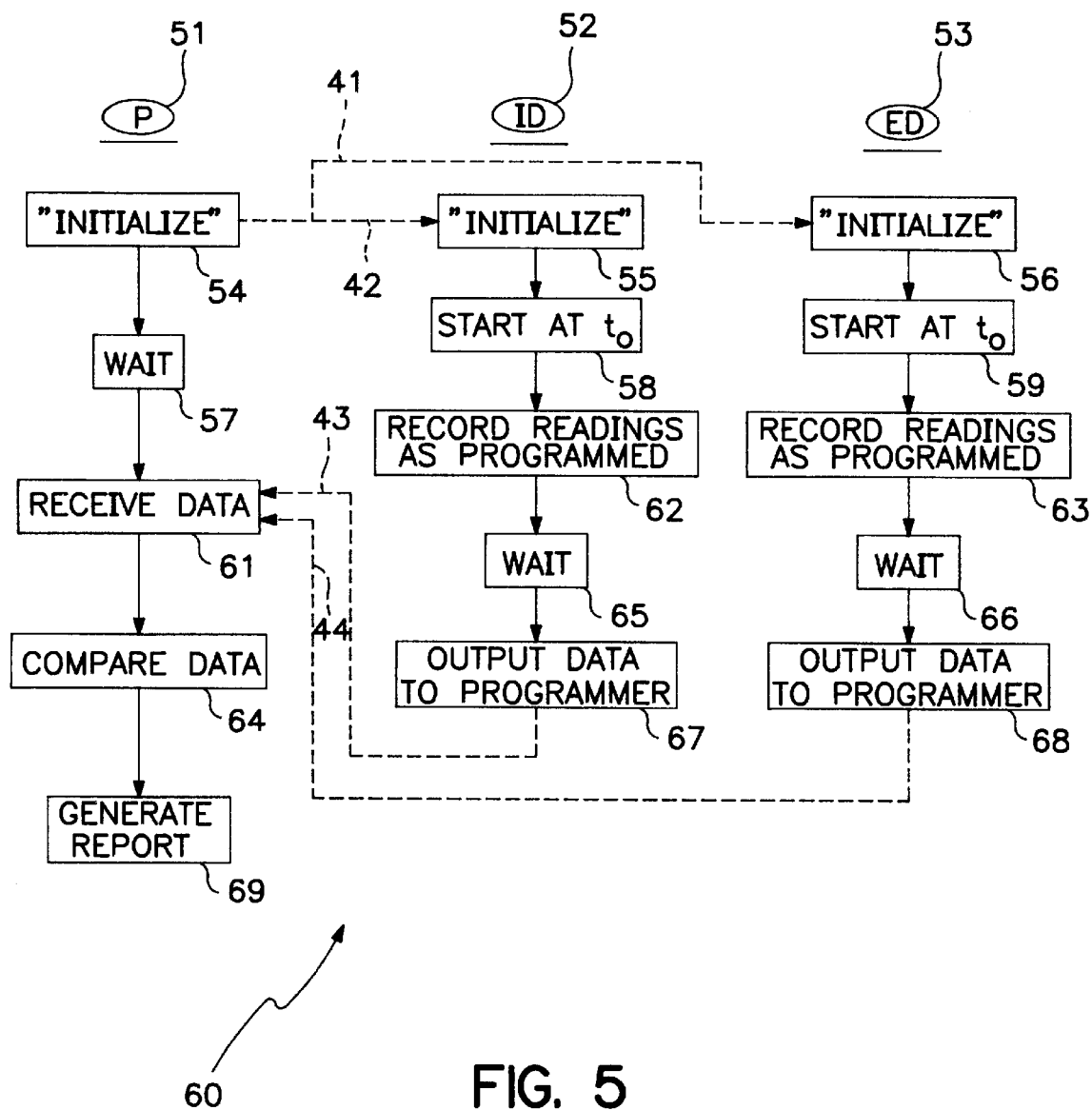
FIG. 5 is a flow diagram for use in describing the coordination of event times as in a preferred embodiment of this invention.

FIG. 5 is a program flowchart 60 having three primary components, one for the programmer designated P (51), one for the implantable device labelled ID (52) and a third for the external device, ED (53).

In general, the programmer can cause the internal and external sensing devices to be initialized at the same time by initialization step 54 which requires communication links to the internal device (42) and the external device (41). Initialization may take many forms as would be known to one of ordinary skill in this art. The presently preferred initialization method uses the on-board clock systems of each of the three devices to coordinate a real time, related time and date indicator. Thus, at a specific time and date both the implantable device and the external device begin recording their respective pressure measurements. The programmer (51) is then disconnected from the external sensing device (57) while the initialized recording sessions of the implantable device (52) and the external device (53) to run their course. The programmer may be used with additional systems or perform other tasks once disconnected.

In blocks 58 and 59, the internal and external devices start at the same time labeled here as $t_0$.

While the easiest implementation would be to simply have both implantable and external device processors record into memory the same type of measurement data at the same time, there are numerous reasons for which users of these devices would prefer to have complementary rather than identical strategies for recording data.

For example, in block 62 it may be advantageous to record both the maximum and minimum ventricular pressure as well as the 75%, 50% and 25% levels of pressure during a single heart beat. For the same time period perhaps only one pressure reading need be recorded during the execution of block 63 by the external device. This time-paired set of readings extending through a test period would generate a most useful histogram for determining exactly what is occurring vis-a-vis the ventricular pressure for this patient. When the period of time for which recording is required has ended, the internal and external devices preferably go into wait states 65 and 66 during which time they await a signal from a device such the programmer 51 indicating that it is ready to receive data (i.e. in block 61) through communications channels 43 and 44. At such time, data is output to the programmer 51, i.e. through blocks 67 and 68.

Within the programmer 51, the data is compared in steps 64 and appropriate adjustments made so that a report can be generated in step 69. This may be simply a visual display on the screen of the programmer or a set of data that may be interpreted by another computerized machine downstream or a printed report, depending upon the desires of the doctor, his patient or the laboratory doing the work.

Figure 6:
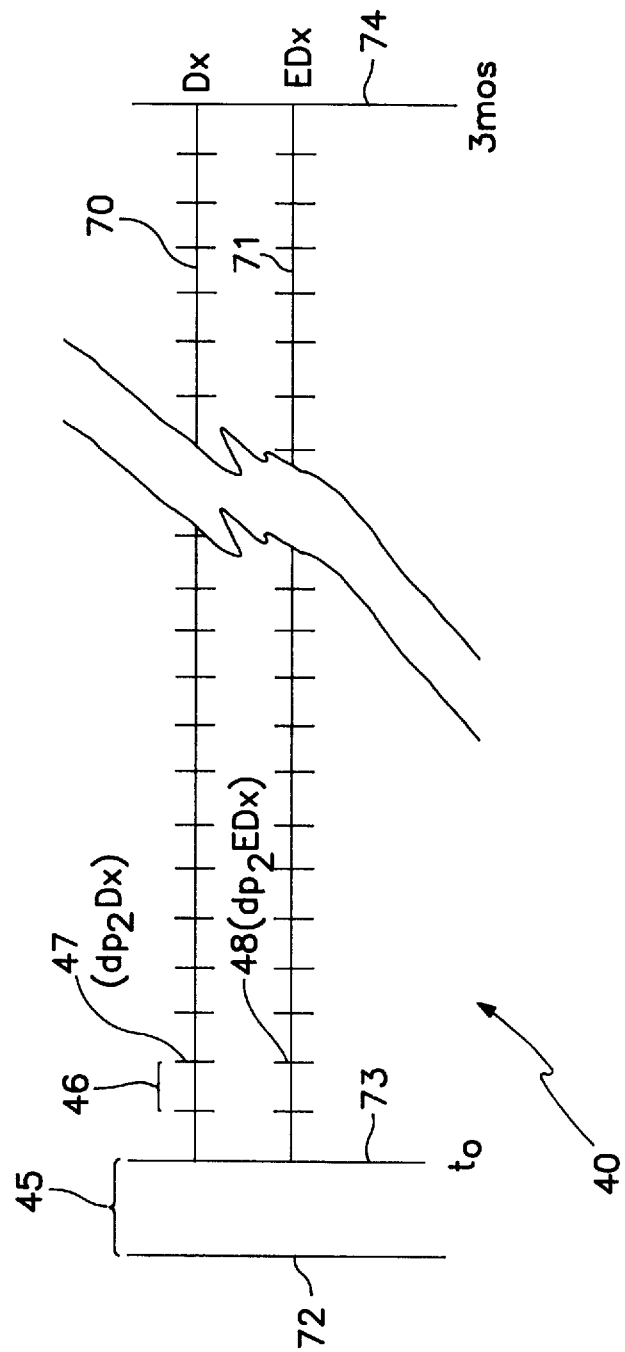
FIG. 6 is a paired chronic time diagram for use in describing the function of a preferred embodiment of this invention.

FIG. 6 describes in a diagrammatic form the collection of data by the internal and external sensor devices. In the graph 40 the external device recording line is identified as $ED_x$ and the internal device recording line as $D_x$. At the time of the beginning of this graph, identified by line 72, and for the interval 45, the doctor sets the patient up with the external and internal devices via the programmer so that initialization occurs such as described with reference to FIG. 5. At time to both devices record for the first time those measurements each device has been programmed to make. Each tick mark (identified as 47, and 48, respectively) along lines 70 and 71 indicate another measurement. The normal spacing for an interval 46 may be adjusted by the doctor or researcher according to his desire for data.

Depending on a given clinical use of the implanted monitor, (acute, medium term, long term) the storage interval in the monitor could be (but is not limited) 2 seconds to an hour.

The storage (or recording) interval in the external pressure recorder would preferably be a constant value dependent on expected rate of changes in ambient pressure, for example, a constant storage rate of one time per minute.

Since the storage rates in the two devices are in the present embodiment not the same, it is necessary for the programmer or report generator to correctly merge the two data sets.

One solution is as follows:

If the storage interval in the implanted monitor is less the than the storage interval in the external device, the single value closest in time from the external device is correlated with a number of samples from the implanted device.

If the storage internal in the implanted monitor is greater than that in the external device the programmer or report generator will average a range of samples from the external device closest in time to the data from the implanted device to correlate with the data from the implanted device.

Also, under some circumstances, the two data sets may not start or end at exactly at the same time. In this situation, the programmer or report generator must only process those records where the data sets overlap temporally.

An example of such a situation follows:

The implanted monitor is set to record for four weeks. The external pressure recorder is started at the same time but the patient does not come to the clinic for six weeks. The data in the implanted device may have "wrapped" such that only the last four weeks worth of data is available. (That is, the capacity of on-board implanted memory is fully stuffed in four weeks and the data which follows writes over the earliest data—a kind of wraparound storage.) In this case the first two weeks of data in the external device must be skipped. If, on the other hand, implanted memory is "frozen" at the end of the first four weeks, the last two weeks of external data would not even be collected internally and so the last two weeks of external data should be discarded.

Thus, an extremely flexible system has been described. It allows for programming at the initiation of recording or prior thereto; of identical or different strategies that are complementary as between internal and external devices. The internal and external devices each have sensors which record and report their measurements. At the end of the recording period the sensor device memory can be discharged into a programmer that will interpret the internal sensor output in light of the external reference sensor readings.

Figure 7:
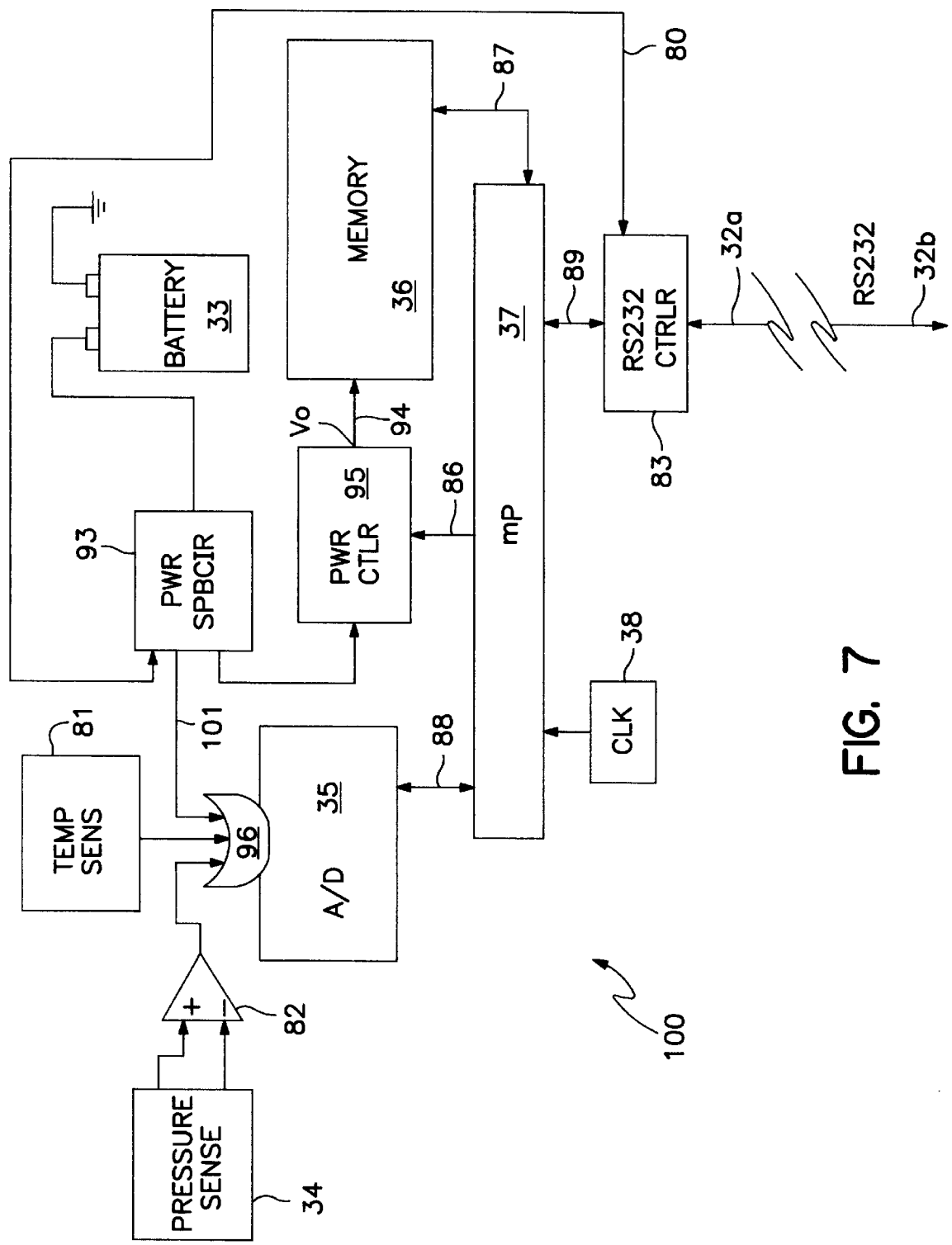
FIG. 7 is a simplified block/circuit diagram in accord with a preferred embodiment of the invention.

Referring now to FIG. 7 in which a circuit block diagram for the preferred embodiment external reference device is shown as Circuit 100, it should be noted that the circuit includes pressure sensor 34, temperature sensor 81, analog to digital coverter 35, microprocessor 37, battery 33, and battery-power stealing and battery circuit 93, a clock 38, and an RS 232 controller block 83. They function as follows:

Power can be supplied and generally is by the battery 33. But in low power conditions, a power stealing circuit is employed (in block 93) which allows power to be taken from the RS232 line that carries the RTS (ready to send) and DTR (data terminal ready) signals. These RTS and DTR signals are set to one or high—meaning there is a voltage in the standard RS232 protocol when the bus is in use. The off-device part of the bus is indicated by reference numeral 32b and the on-device part of the bus by 32a. An RS232 controller 83 provides for data transfers between the RS232 bus and the microprocessor 37 across line 89a, in preferred embodiment as a serial bit stream of data and protocol.

In the preferred embodiment, an on-board clock 38 is distributed through the microprocessor to the other chips on the circuit board to coordinate timing.

The power stealing or battery power circuit 93 provides power to the power controller 95 which the microprocessor 37 can control via line 86 to save power by shutting of memory when not required.

Shown in this diagram also is OR gate 96 attached to the "analog-to-digital" (also called A/D, A-D or A to D) converter 35. An OR gate per se is certainly not required and this illustration is used merely to indicate that the A to D converter 35 of the preferred embodiment accepts one of the three illustrated inputs at a time. Line 101, is one of these inputs and is connected through block 93 to the battery 33 to provide a battery level for the A-D converter 35 to test the battery when microprocessor 37 indicates across line 88 that such is required. The I/O line 88 is also used to communicate the data from the A/D converter 35.

The pressure sensor 34 typically produces a pair of signals, the difference of which indicates the barometric pressure reading before the difference of these signals are generally attracted before an amplifier 82 before being provided as input 2 in an A to D converter such as A/D 35. This is typically called an "instrumentation amp".

In the preferred embodiment a circuit is used including a FET switch to switch from the temperature sensor output from temperature sense circuit 81 to the battery output 101 and vice versa. Nevertheless, there are many forms of multiplexing which could be employed to provide for three inputs to an A-D conversion and all should be covered within the scope of this invention when used in accord with the teachings hereof.

In general then, the A-D converter will typically read and record data from the selected A-D input. Then the data will be read out into the microprocessor and processed into memory as described with reference to 5 and 6. If the circuit is constructed as in accord with the most preferred embodiment herein described, the reading of the temperature sense output can be recorded then the battery check input be read and recorded and the initial reading be subtracted out to derive the offset indicative of the battery voltage level at that time.

If it is desired to have all processing done in either the external or implanted sensor device, a direct communication channel could be established between them and adjustments can be made to the medically relevant output of such an implanted device responsive to such data. For such an embodiment a separate programmer would not be required and coordination of data between the devices would be direct. However, the presently most preferred embodiment assumes no communications between the implanted and the external sensor devices.

Alternative embodiments such as the use of an external pulse oximeter and internal oxygen measuring device or of an implanted temperature sensor and an external one could be employed by one of ordinary skill in the art without undue experimentation from the disclosure above.

Anomalous changes due to extreme varieties (such as a change within 1 minute of 15 mmHg) monitored by one of the sensors can be ignored, assuming appropriate safeguards. So, for example, a power surge that give a false reading may be left out of the data set subject to programmer interpretation.

Venous pressure by a pressure sensor associated with an implantable device could be located in the vein or other location of interest as an obvious adaption of this invention. Accordingly, this invention should not be limited except as set forth in the following claims.

We claim:

1. A system for determining the absolute value of an implanted medical device sensor measurement where said implanted sensor measurement values are subject to significant biasing by external forces in the patient's environment, said system comprising:

a systemwide program for pairing the storage of data sets of sensed values and times between an implanted sensor and measurement device and an external sensor and measurement device and enabling the later comparison of the two data sets, said program having portions thereof stored in memory of system devices for execution therein, said system devices comprising:

a) an implanted sensor and measurement device having a memory for storing sensor data and a portion of said program for execution in said implanted device, a clock, a sensor for generating measurement values and a processor, so arranged and disposed that the memory holds representations of sensor measurement values as coordinated by the processor, said coordinating the enabling of the sensor to generate and the memory to hold each new measurement value at appropriate times in accord with a predetermined processor run and clock driven program, b) an external sensor and measurement device having a memory for storing sensor data and a portion of said program for execution in said external device, a clock, a sensor for generating measurement values and a processor, so arranged and disposed that the memory holds representations of sensor measurement values as coordinated by the processor, said processor coordinating the enabling of the sensor to generate and the memory to hold each new measurement value at appropriate times in accord with a predetermined processor run and clock driven program, c) a coordinating programmer apparatus also having a memory for storing a portion of said program for execution in said apparatus, for initiating timing of paired programs for storing data in said implanted and external devices by way of two communications channels establishable between said programmer and said external device and between said programmer and said implanted device.

2. A system as set forth in claim 1 wherein at least one of said portions of program can be modified by user activities that control said programmer and wherein such modifications can be effected in one of said devices through programmer communication to such device prior to initiating sense gathering activity of the paired programs.

3. A system as set forth in claim 2 wherein one of said portions of program is either loaded into one of said devices, or turned on in one of said devices prior to initiation by said programmer.

4. A system as set forth in claim 1 wherein the implanted device and the external device establish a communications channel between said implanted and external devices for coordinating the initiation of a period for recording measurements by both said implanted and external devices.

5. A system as set forth in claim 4 wherein the communications channel between said programmer and said external device is a data carrying wire cable for conducting electrical signals therebetween.

6. A system as set forth in claim 1 wherein the real-time day and date are used to coordinate timing between the paired data sets of sensed values.

7. A system as set forth in claim 1 wherein each said sensor is a pressure sensor.

8. A system as set forth in claim 1 wherein said coordinating programmer subtracts pressure measurements taken at a given time by said external device from pressure measurements taken by said implanted device from approximately the same time to produce a corrected pressure reading indicative of absolute internal pressure.

9. A process of producing a long term series of gauge pressure readings from within a living body comprising:

measuring over a long term at specified intervals within said long term, internal pressure with an implanted sensor device that measures absolute pressure and recording said measurements with reference to the time they are taken so as to produce a measurement value for each interval, at a time contemporaneous with said long term, and at intervals approximately contemporaneous with said specified intervals, measuring ambient pressure near the living body containing said implanted sensor device and recording said ambient pressure measurements with reference to the time they are taken so as to produce a measurement value for each interval, coordinating the measurements for each approximately specified interval by subtracting the value of the ambient measurement for a given one of the specified intervals from the absolute pressure measurement value from said implanted sensor for the same specified interval, the result of such subtraction being an approximation of the gauge pressure reading for each said specified interval.

10. The process of claim 9, and further comprising the step:

reporting the results of said subtraction as a histogram trend graph for analysis of ventricular pressure with respect to time.

11. A process of producing a chronic histogram of measurement readings from within a living body comprising:

measuring over a long term at specified intervals within said long term, an internally sensed parameter with an implanted sensor device that measures said sensed parameter in absolute terms and recording said measurements with reference to the time they are taken so as to produce a measurement value for each interval, at a time contemporaneous with said long term, and at intervals approximately contemporaneous with said specified intervals, measuring an external and ambient parameter near the living body containing said implanted sensor device and recording said ambient parameter measurements with reference to the time they are taken so as to produce a measurement value for each interval, coordinating the measurements for each approximately specified interval by subtracting the value of the ambient measurement for a given one of the specified intervals from the absolute measurement value from said implanted sensor for the same specified interval, the result of such subtraction being an approximation of the internal measurement for each said specified interval.

12. A system for determining the absolute value of an implanted medical device sensor measurement where said implanted sensor measurement values are subject to significant biasing by changeable external conditions in the environment of the patient, said system comprising:

a) an implanted sensor and measurement device having a memory for storing sensor data, a clock, a sensor for generating measurement values and a processor, so arranged and disposed that the memory holds representations of sensor measurement values as coordinated by the processor, said processor coordinating the enabling of the sensor to generate and the memory to hold each new measurement value at appropriate times in accord with a predetermined processor run and clock driven program, b) an external sensor and measurement device having a memory for storing sensor data, a clock, a sensor for generating measurement values and a processor, so arranged and disposed that the memory holds representations of sensor measurement values as coordinated by the processor, said processor coordinating the enabling of the sensor to generate and the memory to hold each new measurement value at appropriate times in accord with a predetermined processor run and clock driven program, c) a coordinating program in said implanted device which, by way of two communications channels establishable between said implanted and said external device periodically corrects the internal measurement for said external conditions based on the measurement data transferred by said external device to said internal device.

13. A device as set forth in claim 12, and further comprising:

an adaptive program responsive to the corrected internal measurement to adaptively change the functioning of the implanted device.

14. A system for determining the absolute value of an implanted medical device sensor measurement where said implanted sensor measurement values are subject to significant biasing by external forces in the environment of the patient, said system comprising:

a) an implanted sensor and measurement device having a sensor for generating measurement values, a communications channel, and a processor, so arranged and disposed that the memory holds representations of sensor measurement values as coordinated by the processor, said processor coordinating the enabling of the sensor to generate and the communications channel to carry new measurement values at appropriate times in accord with a processor run and clock driven program, b) an external sensor and measurement device having a memory for storing sensor data, a clock, a sensor for generating measurement values and a processor, so arranged and disposed that the memory holds representations of sensor measurement values as coordinated by the processor, said processor coordinating the enabling of the sensor to generate and the memory to hold each new measurement value at appropriate times in accord with a predetermined processor run and clock driven program, c) a coordinating program in said external device which, by way of said communications channel establishable between said implanted and said external device periodically corrects the internal measurement for said external forces based on the measurement data transferred by said external device to said internal device.

* * * * *